US010894957B2

(12) United States Patent
Stray et al.

(10) Patent No.: US 10,894,957 B2
(45) Date of Patent: *Jan. 19, 2021

(54) LYSIS BUFFERS FOR EXTRACTING NUCLEIC ACIDS (71) Applicant: LIFE TECHNOLOGIES CORPORATION, Carlsbad, CA (US)

(72) Inventors: James Stray, San Mateo, CA (US); Jason Yingjie Liu, Foster City, CA (US); Maxim Brevnov, Union City, CA (US); Jaiprakash Shewale, Santa Clara, CA (US); Allison Holt, Burlingame, CA (US)

(73) Assignee: Life Technologies Corporation, Carlsbad, CA (US)

( * ) Notice: Subject to any disclaimer, the term of this patent is extended or adjusted under 35 U.S.C. 154(b) by 47 days.

This patent is subject to a terminal disclaimer.

(21) Appl. No.: 16/013,938

(22) Filed: Jun. 21, 2018

(65) Prior Publication Data

US 2018/0371449 A1 Dec. 27, 2018

Related U.S. Application Data (60) Continuation of application No. 15/235,327, filed on Aug. 12, 2016, now abandoned, which is a division of application No. 12/882,194, filed on Sep. 14, 2010, now Pat. No. 9,447,409.

(60) Provisional application No. 61/379,346, filed on Sep. 1, 2010, provisional application No. 61/360,386, filed on Jun. 30, 2010, provisional application No. 61/243,136, filed on Sep. 16, 2009.

(51) Int. Cl.
C12N 15/10 (2006.01)
C12N 1/06 (2006.01)
C12Q 1/6806 (2018.01)

(52) U.S. Cl.
CPC ........... *C12N 15/1003* (2013.01); *C12N 1/06* (2013.01); *C12N 15/1006* (2013.01); *C12N 15/1013* (2013.01); *C12Q 1/6806* (2013.01)

(58) Field of Classification Search
CPC .. C12N 15/1003; C12N 1/06; C12N 15/1013; C12N 15/1006; C12Q 1/6806
See application file for complete search history.

(56) References Cited

U.S. PATENT DOCUMENTS

| 5,766,852 A | 6/1998 | Down et al. |
| 8,080,645 B2* | 12/2011 | Fischer .................... A61P 31/10 536/23.1 |
| 8,084,443 B2* | 12/2011 | Fischer .................... C12Q 1/70 514/75 |
| 8,357,672 B2* | 1/2013 | Diges ...................... C07H 21/00 514/56 |
| 9,447,409 B2 | 9/2016 | Stray et al. |
| 9,999,217 B2* | 6/2018 | Whitney ............... C12Q 1/6806 |
| 2003/0215845 A1 | 11/2003 | Billie |
| 2005/0106143 A1* | 5/2005 | Giraudon ................ A61P 31/12 424/145.1 |
| 2005/0208510 A1 | 9/2005 | Latham et al. |
| 2006/0078923 A1 | 4/2006 | Mckernan et al. |
| 2006/0188892 A1 | 8/2006 | Latham et al. |
| 2007/0015165 A1 | 1/2007 | Chen et al. |
| 2009/0209751 A1 | 8/2009 | Brevnov et al. |
| 2016/0348092 A1 | 12/2016 | Stray et al. |

FOREIGN PATENT DOCUMENTS

| WO | WO1995/034569 | 12/1995 |
| WO | WO2005/089929 | 9/2005 |
| WO | WO2008/134470 | 11/2008 |
| WO | WO-2011034864 A1 | 3/2011 |

OTHER PUBLICATIONS

Allouche et al., "Genetic identification of decomposed cadavers using nails as DNA source", Forensic Science International: Genetics, vol. 3, No. 1, Dec. 1, 2008, 46-49.
Amory et al., "STR typing of ancient DNA extracted from hair shafts of Siberian mummies", Forensic Science International, Science Direct, vol. 166, Nos. 2-3, Mar. 2, 2007, 218-229.
Anslinger et al., "Application of the BioRobot EZ1 in a forensic laboratory", Legal Medicine, vol. 7, No. 3, May 1, 2005, 164-168.
Anslinger et al., "Identification of the skeletal remains of Martin Bormann by mtDNA analysis", International Journal of Legal Medicine vol. 114, Jan. 1, 2001, 194-196.
Applied Biosystems, "Testing the Effectiveness of the PrepFiler Kit for DNA Extraction from Forensic Samples (An Overview of Test Site Data)", Forensic News: Customer Corner, Jul. 1, 2008, 1-9.
Barbisin et al., "Assessment of DNA extracted from forensic samples prior to genotyping.", Forensic Science Review, vol. 22, No. 2, Jul. 2010, 199-214.
Broemeling, "An Instrument for Automated Purification of Nucleic Acids from Contaminated Forensic Samples", Journal of the Association for Laboratory Automation (JALA), vol. 13, No. 1, Feb. 2008, 40-48.
Coble, et al., "Mystery solved: The identification of the two missing Romanov children using DNA analysis"; PLoS One 4: e4838; 2009.
Duval, "Optimized manual and automated recovery of amplifiable DNA from tissues preserved in buffered formalin and alcohol-based fixative", Forensic Science International: Genetics, vol. 4, No. 2, Jul. 8, 2009, 80-88.

(Continued)

*Primary Examiner* — Joseph G. Dauner
(74) *Attorney, Agent, or Firm* — Workman Nydegger (57) ABSTRACT

The present teachings relate to the extraction of nucleic acid from solid materials. Provided are useful compositions, methods and kits for obtaining nucleic acids from a solid biological sample or an adhesive material having a biological material adherent or embedded within the adhesive substrate. The extracted nucleic acid can be used in downstream applications such as genotyping, detection, quantification, and identification of the source of the biological material.

4 Claims, 1 Drawing Sheet

(56) References Cited

OTHER PUBLICATIONS

Graham et al., "Can post-mortem blood be used for DNA profiling after peri-mortem blood transfusion?", International Journal of Legal Medicine, vol. 212, No. 1, Dec. 10, 2007, 18-23.
Irwin et al., "DNA identification of "Earthquake McGoon" 50 years postmortem", J Forensic Sci 52:1115, 2007,.
Ishiko, et al., "Experimental studies on identification of the driver based on STR analysis", Legal Medicine vol. 10, No. 3, Nov. 2, 2008, 115-118.
Loreille et al., High efficiency DNA extraction from bone by total demineralization; Forensic Sci Int Genet 1:191; 2007.
Mulero et al., "Development and validation of the AmpFlSTR MiniFiler PCR Amplification Kit: a MiniSTR multiplex for the analysis of degraded and/or PCR inhibited DNA", Journal of Forensic Science, vol. 53, No. 4, Jul. 2008, 838-852.
PCT/US2010/048833, International Search and Written Opinion Report, dated Nov. 23, 2010.
Rohland et al., "Comparison and Optimization of Ancient DNA Extraction", BioTechniques, vol. 42, No. 3, Mar. 1, 2007, 343-352.
Stray et al., "Extraction of DNA from forensic biological samples for genotyping", Forensic Science Review vol. 22, No. 2 Jul. 2010 , 159-175.
Stray et al., "Extraction of DNA from Human Remains", Forensic Science Review, vol. 22, No. 2, Jul. 2010, 177-185.
Stray et al., "Extraction of high quality DNA from biological materials and calcified tissues", Forensic Science International: Genetics Supplement Series vol. 2, 2009, 159- 160.

\* cited by examiner

PO stands for PCR positive control

LYSIS BUFFERS FOR EXTRACTING NUCLEIC ACIDS

CROSS-REFERENCE TO RELATED APPLICATIONS

This application is a Continuation of U.S. application Ser. No. 15/235,327 filed Aug. 12, 2016, which is a Divisional of U.S. patent application Ser. No. 12/882,194 filed Sep. 14, 2010 (now U.S. Pat. No. 9,447,409), which claims benefit of U.S. Provisional Application No. 61/243,136 filed Sep. 16, 2009, U.S. Provisional Application No. 61/360,386 filed Jun. 30, 2010, and U.S. Provisional Application No. 61/379,346 filed Sep. 1, 2010, all which are hereby incorporated by reference in their entirety.

FIELD

In general, the present teachings relate to the extraction of nucleic acid from solid materials such as bone, tooth and calcified tissues, or biological samples embedded or adherent to adhesive materials or denim materials.

BACKGROUND

The extraction of nucleic acid from solid biological materials such as calcified bone and tooth, or biological samples containing nucleic acids embedded and/or adherent to adhesive and gum-containing materials as well as biological materials on dried or embedded in denim materials presents sample processing challenges and potential delays in sample processing in the forensic laboratory. Forensic samples, missing person, ancient and degraded samples also have the added complication of having PCR inhibitors potentially extracted with the eluted nucleic acid. The present teachings provide useful compositions and methods for obtaining nucleic acids, such as genomic DNA and RNA, from a solid biological sample, an adhesive material having a biological material adherent or embedded within the adhesive substrate or a denim materials or soil. The extracted nucleic acid can be used in downstream applications such as genotyping, detection, quantification, and identification of the source of the biological material where molecular biological processes such as PCR are utilized. The lysis solutions provided can be used to prepare high quantities of nucleic acid, such as DNA and preserve the DNA integrity extracted from calcified tissues, or biological tissues on gum and/or adhesive substrates and materials, and denim substrates and materials. The solutions provide highly efficient methods for DNA extraction as well methods for the removal of PCR inhibitors and methods to preclude extraction of PCR inhibitors. Furthermore, the procedure for extraction and purification of nucleic acids is fully automatable, using standard liquid handling systems.

The section headings used herein are for organizational purposes only and are not to be construed as limiting the described subject matter in any way. All literature cited in this specification, including but not limited to, patents, patent applications, articles, books, and treatises are expressly incorporated by reference in their entirety for any purpose. In the event that any of the incorporated literature contradicts any term defined herein, this specification controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

SUMMARY OF SOME EMBODIMENTS OF THE INVENTION

In some embodiments, disclosed is a composition for lysing a solid having adherent or embedded within biological material. The lysis reagent solution having a composition having one or more of a detergent, a chelating agent, a reducing agent, and an enzyme. The detergent can be an anionic detergent, an ionic detergent or a combination thereof. The detergent can be one or more of N-lauroyl sarcosine (NLS, also known as sarcosyl or sodium lauroyl sarcosinate), sodium deoxycholate, CTAB, dodecyl β-D-maltoside, nonanoyl-N-methylglucamide, polyethylene glycol p-(1,1,3,3-tetramethylbutyl)-phenyl ether, sodium dodecyl sulfate (SDS), and combinations thereof. The chelating agent can be one or more of ethylene glycol tetraacetic acid (EGTA) and ethylene diamine tetraacetic acid (EDTA), citric acid and combinations thereof. The reducing agent can be one or more of tris(2-carboxyethyl) phosphine (TCEP) dithioerythritol (DTE), and dithiothreitol (DTT). The enzyme can be one or more of caspase, chymotrypsin, pepsin, proteinase K, thrombin, *Staphylococcus* V8 protease, pronase, papain, *Bacillus* sp. E1A protease, and trypsin. The salt can be one or more of sodium chloride, potassium chloride, magnesium chloride, manganese chloride as well as fluorinated and iodinated forms thereof. The lysis solution can have a pH ranging from 5.0-12.0, or 5.1, 6.0, 7.0, 8.0, 9.0, 10.0, and 11.0 as well as intervals within each whole number.

In some embodiments, the solid sample lysed by the lysing solution has nucleic acid. The solid can be a biological material, an adhesive substrate, or a natural or synthetic substrate. In some embodiments, the biological material can be bone, cartilage, ligament, tendon, and tooth. In some embodiments the adhesive material can be chewing gum, cigar butt, cigarette butt, adhesive film, adhesive label, adhesive paper, adhesive skin patch, envelope, envelope flap, stamp, e.g., a postage stamp, and adhesive tape. In some embodiments, a biological sample can be embedded or adhered to the adhesive material.

In various embodiments, the adhesive skin patch is selected from the group consisting of electronic electrode, transferable tattoo, transdermal chemical substance patch and wound care dressing. And, the adhesive tape can be an adhesive bandage, athletic tape, wrapping tape, duct tape, electrical tape, hair tape, a fingerprint tape lift and so on.

In some embodiments, disclosed are methods for making a product that comprises a nucleic acid using the disclosed lysis solution. The method includes incubating a solid sample in the lysis solution and extracting a supernatant in which the nucleic acid has been extracted from the solid sample. The solid sample can be a biological material such as bone, cartilage, ligament, tendon, and tooth, an adhesive material such as chewing gum, cigar butt, cigarette butt, adhesive film, adhesive label, adhesive paper, adhesive skin patch, envelope, envelope flap, stamp, a fingerprint tape lift, and adhesive tape, a denim material. In some embodiments, the method can also include shaking and/or vortexing the solid sample in the lysis solution while the mixture is incubated, centrifuging the solid sample in the lysis solution after incubation, lysing the biological sample, biological material and/or solid sample in the lysis solution to form a lysate having nucleic acid and extracting the lysate to obtain a product with nucleic acid.

In other embodiments, disclosed are methods of separating a nucleic acid from a solid in which the solid is lysed by the lysis solution and the lysate is centrifuged to separate the solid from the nucleic acid which remains in the supernatant. In some embodiments, the method can also include shaking the solid with the lysis solution and extracting the lysate to obtain a product with nucleic acid separate from the solid.

In other embodiments, the nucleic acid recovered from a fingerprint tape lift using the methods described herein can be used for identification of the organism from which the biological material was obtained. The nucleic acid can be used in genotyping assays for STRs, HLA markers and RFLP typing, Y-STR and Y-SNP typing, mtDNA sequencing, and insertion/deletion polymorphisms typing. In conjunction with or separate to the genotyping assays for identification purposes the fingerprint can be used for comparison to a fingerprint collection and/or a database of fingerprints.

Other embodiments include kits for extracting nucleic acid from a solid such as a biological material, an adhesive material or substrate, and denim material or substrates having epithelial, blood, semen, saliva or other biological fluids known to one of skill in the art. The kit has at least one of a first detergent, a chelating agent, a reducing agent, and an enzyme either as separate solutions of each or in combinations. In some embodiments, the kit can also have optional solutions such as a solution having a polymer. The polymer comprises one or more of dextran, cellulose, cellulose derivatives, soluble starch, dextrin, cellodextrin, polyethylene glycol, heparin, glycogen, and combinations thereof. The kit can also have a second detergent, a wash solution, a second wash solution, DNase free water, a magnetic device, and magnetically attractable particles comprising dextran-encased magnetic nanoparticles. It should be understood that a given embodiment need not have all aspects and features described herein. It should be understood that these aspects and embodiments are merely exemplary and explanatory and are not restrictive of the invention.

Applicants have provided embodiments for nucleic acid extraction methods from samples containing minute nucleic acid quantities. Embodiments of such methods are rapid, eliminate use of strong organic solvents, simplify processing and reduce sample handling and risks of cross-contamination with improved user safety.

These and other features of the present teachings are set forth herein.

DESCRIPTION OF EXEMPLARY EMBODIMENTS

For the purposes of interpreting of this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). It is noted that, as used in this specification and the appended claims, the singular forms "a," "an," and "the," include plural referents unless expressly and unequivocally limited to one referent. The use of "or" means "and/or" unless stated otherwise. For illustration purposes, but not as a limitation, "X and/or Y" can mean "X" or "Y" or "X and Y". The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of". The term "and/or" means one or all of the listed elements or a combination of any two or more of the listed element.

U.S. patent application Ser. Nos. 10/306,347, 11/789,352 and 60/334,029 are incorporated by reference herein in their entirety for any purpose.

The practice of the present invention may employ conventional techniques and descriptions of organic chemistry, polymer technology, molecular biology (including recombinant techniques), cell biology, biochemistry, and immunology, which are within the skill of the art. Such conventional techniques include oligonucleotide synthesis, hybridization, extension reaction, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as Genome Analysis: A Laboratory Manual Series (Vols. I-IV), PCR Primer: A Laboratory Manual, and Molecular Cloning: A Laboratory Manual (all from Cold Spring Harbor Laboratory Press, 1989), Gait, "Oligonucleotide Synthesis: A Practical Approach" 1984, IRL Press, London, Nelson and Cox (2000), Lehninger, Principles of Biochemistry $3^{rd}$ Ed., W. H. Freeman Pub., New York, N.Y. and Berg et al. (2002) Biochemistry, $5^{th}$ Ed., W. H. Freeman Pub., New York, N.Y. all of which are herein incorporated in their entirety by reference for all purposes.

As used herein, the term "adhere" refers to the bond between at least two items or surfaces or the binding of at least two items or surfaces together. The bond can be a fusing, gluing, or sticking together of the at least two items or surfaces.

As used herein, the term "adhesive" refers to a substance capable of binding at least two items. The adhesive can be a cement, glue, paste, starch, gum or chemical compound or polymer from a natural or synthetic source and can be applied to an envelope, film, label, paper, patch, stamp or tape as one of the at least two items. The adhesive can be a liquid or a solid or form a solid upon drying by evaporation or heating, ultra-violet light curing, or other physical means. The first item can have the adhesive integral to it, e.g., gum or applied to it, e.g., tape. Alternatively, the first item comprises the adhesive such that the first item can be bound in a removable, temporary, semi-permanent or permanent status with respect to the bond it forms with an at least second item. The adhesive can be made soluble or be made sticky by the application of a liquid such as saliva. For example, when a stamp is licked by a tongue prior to its application to an envelope. Another example can be the flap of an envelope which when licked, such that the adhesive on the flap of the envelope becomes sticky and then when folded over to close the envelope opening, creates a seal due to the adhesive holding the envelope flap in constant, virtually permanent, contact with the envelope.

As used herein, the terms "adhesive material" and "adhesive substrate" are used interchangeably and refer to items containing or have integral to its composition an adhesive, sticky surface or adhesive composition, e.g., chewing gum, cigar butt, cigarette butt, adhesive film, adhesive label, adhesive paper, adhesive skin patch, envelope flap, stamp, an adhesive tape used for lifting fingerprints, biological, organic or inorganic materials and adhesive tape.

As used herein, the term "adhesive film" refers to a thin flexible sheet that can adhere to an item. The film can be permanently adhered to the item or is removable.

As used herein, the term "adhesive label" or "adhesive sticker" refers to an item having identifying information or design on an upper surface that can adhere to another item or surface by the surface opposite the identifying information or design. The label can permanently adhere to the other item or is removable.

As used herein, the term "adhesive paper" refers to a paper (cellulose, wood pulp derived, vinyl, plastic or synthetic paper) with an adherent surface that forms a removable, temporary, semi-permanent or permanent bond with respect to the surface to which it is attached, e.g., envelope, postage stamp, re-adherable stationary or sticky note, or sticker.

As used herein, the term "adhesive skin patch" refers to a round, oval, rectangular or other shape that can adhere in a removable fashion to an intact or damaged (wound) dermal surface, e.g., an EKG electrode, a transferable tattoo, a nicotine patch, and a plaster.

As used herein, the term "adhesive tape" refers to a flexible strip or band that can adhere to another item or surface, e.g., athletic tape, wrapping tape, Scotch® brand tape. The tape can be permanently adhered to the other item or removable. The tape can be soluble or insoluble in an aqueous or organic solution.

As used herein, the term "biological material" refers to blood, mucus, semen, saliva, skin tissue, bone, cartilage, ligament, tendon, tooth, fingerprint, etc. The biological material can be a calcified, hardened, solid and a natural composition of biological origin. The biological material can have a solid, fluid, tissue or cells comprising nucleic acid. The biological material can include but is not limited to, nucleic acid comprising material recovered from an adhesive and/or sticky material including, but not limited to, chewing gum, cigar butt, cigarette butt, adhesive film, adhesive label, adhesive paper, adhesive skin patch, envelope, envelope flap, stamp, a fingerprint tape lift and adhesive tape.

As used herein, the term "biological sample" refers to a biological material adherent to or imbedded in an adhesive material, e.g., blood, mucus, semen, saliva, skin cell, skin tissue, bone, cartilage, ligament, tendon, tooth, a fluid, tissue or cells. The biological sample comprises nucleic acid.

As used herein, "DNA" refers to deoxyribonucleic acid in its various forms as understood in the art, such as genomic DNA, cDNA, isolated nucleic acid molecules, vector DNA, and chromosomal DNA. "Nucleic acid" refers to the nucleic acid molecule or molecules, DNA or RNA (ribonucleic acid) in any form. As used herein, the term "nucleic acid molecule" or "extracted nucleic acid" refers to a nucleic acid molecule (DNA or RNA of any form) that has been recovered from its native environment. Some examples of extracted nucleic acid molecules are partially or substantially purified nucleic acid molecules, nucleic acids obtained from forensic and other samples comprising biological material, such as blood, mucus, semen, saliva, skin tissue, bone, cartilage, ligament, tendon, and tooth, etc. Also envisioned is biological material recovered from an adhesive and/or sticky material including but not limited to, chewing gum, cigar butt, cigarette butt, adhesive film, adhesive label, adhesive paper, adhesive skin patch, envelope, stamp, and adhesive tape, as well as in nucleic acid samples derived from archeological, crime scene processing, forensic, human identification, natural and mass disaster scenes collected by forensic, crime, research, search and rescue, and recovery methods and techniques.

As used herein, the terms "fingerprint" and "fingerprint image" are used interchangeably herein and refer to friction skin ridge impressions made when the epidermal ridges and indentations of the skin found on a ventral surface of a digit, including but not limited to, fingers and toes, a thumb, as well as a palm and a sole of a foot, contact a surface.

As used herein, the term "genomic DNA" refers to the nucleic acids comprising the chromosomal DNA sequence of a gene or segment of a gene, including the DNA sequence of noncoding as well as coding regions. Genomic DNA also refers to DNA isolated directly from biological samples e.g., bone, tooth, tissue, cells or chromosomes or the cloned copies of all or part of such DNA. Genomic DNA also refers to DNA extracted from an adhesive or sticky material e.g., chewing gum, cigar butt, cigarette butt, adhesive film, adhesive label, adhesive paper, adhesive skin patch, envelope, stamp, and adhesive tape. Gum can be of natural or synthetic origin. Natural gum can be latex, gum Acacia, Guar gum, Chicle and Chicle varieties such as chicoo and chicozapote. Synthetic gum can be polyisobutylene.

As used herein, the terms "denim material" and "denim substrate" are used interchangeably and refer to materials of either animal or vegetable origin. The denim material composed entirely of cotton or cotton blended with natural or synthetic fibers. The cotton denim fabric can include but is not limited to blue, dark blue, black, stone-washed, acid washed and the like.

As used herein, the terms "polynucleotide", "oligonucleotide", and "nucleic acid" are used interchangeably herein and refer to single-stranded and double-stranded polymers of nucleotide monomers, including without limitation 2'-deoxyribonucleotides (DNA) and ribonucleotides (RNA) linked by internucleotide phosphodiester bond linkages, or internucleotide analogs, and associated counter ions, e.g., $H^+$, $NH_4^+$, trialkylammonium, $Mg^{2+}$, Nat, and the like. A polynucleotide may be composed entirely of deoxyribonucleotides, entirely of ribonucleotides, or chimeric mixtures thereof and can include nucleotide analogs. The nucleotide monomer units may comprise any nucleotide or nucleotide analog. Polynucleotides typically range in size from a few monomeric units, e.g. 5-40 when they are sometimes referred to in the art as oligonucleotides, to several thousands of monomeric nucleotide units. Unless denoted otherwise, whenever a polynucleotide sequence is represented, it will be understood that the nucleotides are in 5' to 3' order from left to right and that "A" denotes deoxyadenosine, "C" denotes deoxycytosine, "G" denotes deoxyguanosine, "T" denotes thymidine, and "U" denotes deoxyuridine, unless otherwise noted.

As used herein, the term "solid" refers to a material that is not a liquid such as an adhesive containing material as well as hardened, dense materials having a matrix such as calcified biological materials e.g., bone, tooth, as well as cartilage, tendon and ligament and common dust which is composed of sloughed skin cells. The solid can contain or is suspected of containing a nucleic acid.

As used herein, the term "solid sample" refers to a hard, dense material, likely a biological material such as bone, cartilage, ligament, tendon and tooth or an adhesive material that is nonporous and/or water insoluble and contains or is suspected of containing a nucleic acid.

Also herein, the recitations of numerical ranges and numerical ranges by endpoints include all numbers subsumed within that range (e.g., 1 to 5 includes 1, 1.5, 2, 2.75, 3, 3.80, 4, 5, etc.).

In some embodiments of the present teachings, compositions, methods and kits are described in which nucleic acid molecules can be separated and/or extracted from samples and, in some embodiments, in which the product made from the compositions, methods and kits are nucleic acids. In some embodiments, the compositions, methods and kits of the present teachings result in the formation of a product which comprises the extracted nucleic acid.

In some embodiments of the present teachings, compositions are provided wherein a sample can be treated with a lysis solution comprising at least one each of a detergent, a chelating agent, a reducing agent, and an enzyme, and combinations thereof in order to extract nucleic acid molecules from the sample. In various embodiments, the sample can comprise one or more of free nucleic acids; extracted from solid matrices including, but not limited to, biological materials such as bone, cartilage, ligament, tendon, and tooth, and so on. In various embodiments, the sample can comprise nucleic acid extracted from adhesive materials, including, but not limited to, materials such as chewing gum, cigar butt, cigarette butt, adhesive film, adhesive label, adhesive paper, adhesive skin patch, envelope flap, stamp, a fingerprint tape lift and adhesive tape. In some embodiments, the sample can comprise nucleic acid extracted from denim materials including, but not limited to, denim fabric including blue, dark blue, black, stone-washed, acid washed and the like. In additional embodiments of the present teachings, methods are described wherein a nucleic acid can be extracted from a sample, comprising the steps of incubating the sample with a solution comprising one or more of a detergent, a chelating agent, a reducing agent, a salt and an enzyme; and extracting the supernatant. The incubation can be at room temperature, 35° C., 40° C., 41° C., 42° C., 43° C., 44° C., 45° C., 50° C., 51° C., 52° C., 53° C., 54° C., 55° C., 56° C., 57° C., 58° C., 59° C., 60° C., 65° C. and 70° C., as well as intervals therein. Such methods may further comprise the steps of centrifuging the incubation solution to remove solids from the supernatant and treating the supernatant to isolate the nucleic acids.

The nucleic acids thus obtained can then be utilized in any of various downstream applications and analyses such as, for example, quantification, detection, and genotyping of specific nucleic acids or even of a biological species. These analyses can be performed, for example, by PCR amplification. As one example, in forensic DNA analysis the human nuclear DNA (nDNA) and/or genomic DNA can be obtained from complex biomaterials and then genotyped using PCR. As another example, a DNA preparation can be used for quantification of human DNA, or more specifically human male DNA, using real-time PCR systems such as QUANTIFILER® or QUANTIFILER DUO® kits (Applied Biosystems/Life Technologies Corp., Foster City, Calif.), and/or genotyped for autosomal or Y-chromosomal short tandem repeat loci using systems such as, for example, AMPFISTR® kits. Based upon the amount of DNA present in a sample, a particular genotyping system can be selected that will yield the best results for the particular analysis required. Therefore, in order to best utilize nucleic acids in downstream applications, it is particularly desirable that the extraction and isolation methods result not only in a product of high yield, but also one that is relatively free of inhibitors of downstream applications such as PCR. The nucleic acids analyzed by quantification, detection, and genotyping can be used in the identification of the source of the nucleic acid.

Typically, forensic evidence samples are variable in sample types, substrate or matrix wherein the biological materials are embedded, including but not limited to, solid biological samples or the surface upon which the forensic sample was collected, which can result in sample exposure to environmental insults, contamination by PCR inhibitors and limit the quantity of starting sample material. Extraction of nucleic acid, including, but not limited to, DNA from forensic evidence samples, often exposed to temperature variation, excessive moisture or dehydrating conditions, and sample contaminants as would be known to one of ordinary skill in the art during acquisition and processing, can lead to difficulties in isolation of nucleic acid and the potential of contamination with compounds, e.g., dye or other chemical treatments of denim fabric that act to inhibit PCR, and which therefore interfere with attempts at genotyping or other analyses. It is desirable to improve extraction processes and in so doing, remove inhibitors during the isolation of nucleic acid, such as DNA or RNA for use in forensic analysis, prior to use in subsequent processes employing enzymes, such as, amplification.

As an example, forensic samples can employ adhesive materials in sample collection or be a component of the sample itself. The presence of the adhesive often decreases the overall recovery of nucleic acid as the adhesive can interfere with the isolation process as when particulates are used to isolate the nucleic acid. In examples present below it was shown that nucleic acid extracted from cigarette butts, chewing gum, and dried blood, saliva and biological material (including skin cells and cells from a fingerprint) in a tape lift resulted in higher nucleic acid recoveries and was free of PCR contaminants when profiled by short tandem repeat (STR) analysis.

Another example of difficult forensic samples are solid biological materials including, but not limited to, calcified tissues such as bone and tooth. The dense matrix requires lengthy, labor intensive processes, often lasting more than 24 hours, before minute amounts of nucleic acid are extracted. The disclosed teachings achieved maximum recovery of DNA by disruption of the calcified matrix so that the majority of the biological material is exposed to the lysis reagent solution. The yield of DNA from bone and tooth samples is summarized in Table 1. In examples to follow the time required to extract nucleic acid from bone and tooth at optimum yield was achieved after only two hours. Because the disclosed lysis solution compositions and methods for extracting nucleic acid results in improved and faster DNA recovery, the amount of DNA present in a sample can be detected with greater sensitivity by real-time PCR methods known to one of skill in the art.

Various embodiments of the present teachings relate to efficient extraction of nucleic acids such as, for example, genomic DNA in such a quantity that subsequent isolation and elution of the nucleic acid using the PREPFILER™ Forensics DNA Extraction Kit (P/N 4392852 or 4392353, Applied Biosystems, Foster City, Calif.) provides nucleic acid suitable for DNA quantification and analyses. Embodiments of these teachings thus enable effective extraction of nucleic acids, such as genomic DNA, from various solid types of biological materials, adhesive comprising materials as well as biological fluid samples from denim. In addition, nucleic acids such as genomic DNA can be isolated from either small or large quantities of the biological materials that are commonly processed in laboratories such as, for example, those involved in genotyping analyses.

Embodiments of the lysis solution provided herein can comprise a mixture of a chelating agent (preferably ranging from 250-500 mM), such as ethylene glycol tetraacetic acid (EGTA) and/or ethylene diamine tetraacetic acid (EDTA) and/or citric acid; detergents (preferably ranging from 0.1% to 3%), such as at least one of N-lauroyl sarcosine, sodium deoxycholate, CTAB, N-dodecyl β-D-maltoside, nonanoyl-N-methylglucamide, Triton® X-100, NP-40, and/or sodium dodecyl sulfate; a salt (ranging from 50 mM to 500 mM), such as sodium chloride, potassium chloride, magnesium chloride, manganese chloride as well as fluorinated and iodinated forms thereof; and reducing agent (preferably ranging from 10 to 100 mM), such as tris(2-carboxyethyl) phosphine (TCEP) dithioerythritol (DTE), and dithiothreitol (DTT), and an enzyme (preferably ranging from 0.5 to 1 mg/mL), such as at least one of caspase, chymotrypsin, pepsin, proteinase K, thrombin, *Staphylococcus* V8 protease, pronase, papain, *Bacillus* sp. E1A protease, and trypsin. Tables provided below indicate the extraction efficiency as a comparison of various incubation times in the lysis solution, quantity and type of starting solid, adhesive or denim material. The lysis solution extracts the nucleic acid from the solid matrices or adhesive material such that the nucleic acid supernatant can be isolated and cleansed of impurities using the PrepFiler™ Kit.

These embodiments and other features of the present teachings will become more apparent from the description herein.

Various embodiments of the present teachings relate to a lysis solution and methods of using the solution, amenable to assembly in a kit, for the extraction of nucleic acids including, but not limited to, genomic DNA, from adhesive materials containing biological samples and solid samples, such as biological samples, thought to contain or known to comprise nucleic acid. The adhesive material can be for example, a tape lift collected by forensic methods, e.g., a dried blood, saliva and fingerprint, as well as an envelope flap, stamp, including but not limited to a postage stamp, trading stamp, hunting license stamp, conservation stamp, chewing gum, cigar butt, cigarette butt, adhesive film, adhesive label, adhesive paper, adhesive skin patch, envelope, stamp, and adhesive tape and such. The adhesive material is thought to contain nucleic acid attached or embedded in the adhesive material and the present teachings relate to the extraction of the nucleic acid, if present, from the adhesive material sample. Adhesive material has been shown to interfere with subsequent nucleic acid isolation, purification and overall yield when using the PrepFiler™ kit. The adhesive interferes with the handling of the magnetic particles, in the polymer-nucleic acid-magnetic particle complex formed in the PrepFiler protocol. The formation of the complex is such that the polymer entraps the nucleic acid, polymer attaches to magnetic particles, and so indirectly connects the nucleic acid with the magnetic particles until the complex is washed to remove contaminants and inhibitors such that the nucleic acid is amendable to use in downstream applications, such as PCR. Obtaining nucleic acid from the adhesive containing sample was difficult, tedious and of low yield prior to the development of the lysis solution taught herein.

The dyes, pigments and fibers found in denim fabric as is used in the manufacture, including, but not limited to blue jeans, skirts and jackets, has been found to inhibit STR analysis of nucleic acids isolated therefrom in genotyping assays such as the Identifiler® kit (Applied Biosystems). The fibers appear to complex with the pigments or dyes and interferes with the handling of the magnetic particles, in the polymer-nucleic acid-magnetic particle complex formed in the PrepFiler protocol. This has made obtaining nucleic acid from the denim sample compromised by PCR inhibitors, DNA recovery is difficult, tedious and of low yield prior to the development of the Tris-Cl lysis solution taught herein.

Various embodiments of the present teachings relate to a nucleic acid extraction, such as for genomic DNA, comprising lysis solution, methods and kits for extraction of the nucleic acids from solid biological samples, including, but not limited to, bone, cartilage, ligament, tendon, and tooth, and adhesive. Embodiments of these methods can comprise: cleaning the solid sample with a mild detergent solution, air-drying overnight, removing the exterior layer with a sanding stone, and pulverizing the sample. The prepared sample is then incubated with lysis solution such that the nucleic acid containing cells are released from the solid matrix. The solid biological material contains nucleic acid and the present teachings relate to the extraction of the nucleic acid from the solid material. Calcified and hardened biological materials have been shown to provide low yields of nucleic acid when using the PrepFiler™ kit (Applied Biosystems, Foster City, Calif.), because the solid matrices provide unique challenges for the extraction and isolation of nucleic acid. The yield of nucleic acid from the solid biological material has been improved by use of the lysis solution taught herein prior to the PrepFiler protocol.

Standard nucleic acid isolation techniques, including cell lysis, and washing and elution of nucleic acids, are well known in the art and unless otherwise noted, can be carried out according to various techniques as described, for example, in *DNA Typing Protocols: Molecular Biology and Forensic Analysis,* 1$^{st}$ edition, B. Budowle et al., eds., Eaton Publishing Co. (2000); J M Butler, *Forensic DNA Typing: Biology, Technology, and Genetics of STR Markers,* 2$^{nd}$ edition, Elsevier Academic Press (2005); or P. Gill, "Application of Low Copy Number DNA Profiling," Croatian Medical Journal 42:229-232 (2001); F R Bieber et al., "Isolation of DNA from Forensic Evidence," *Current Protocols in Human Genetics,* Supplement 26 (2000); *Forensic DNA Profiling Protocols, Methods in Molecular Biology,* vol. 98, P J Lincoln and J. Thomson, eds., Humana Press (1998).

Applicants have discovered that nucleic acids are more easily isolated and purified when using the PrepFiler protocol for nucleic acid containing adhesive materials and solid biological samples by using the lysis reagent solution taught herein having one or more of a detergent, a chelating agent, a reducing agent, a salt, and an enzyme. The lysis solution improves the efficiency and yield of nucleic acids, such as genomic DNA, from adhesive materials, solid biological samples. The detergent can be ionic or anionic. Some examples of appropriate detergents include, but are not limited to, N-lauroyl sarcosine (NLS), lauroyl sarcosinate, also known as sarcosyl, an ionic surfactant derived from sarcosine; hexadecyltrimethylammonium bromide or cetyltrimethylammonium bromide (CTAB); deoxycholate; sodium citrate; sodium deoxycholate; dodecyl β-D-maltoside; nonanoyl-N-methylglucamide; sodium dodecyl sulfate; polyethylene glycol p-(1,1,3,3-tetramethylbutyl)-phenyl ether (commercially known as Triton® X-100); and combinations thereof. In some embodiments, the detergent comprises NLS in the range of 0.5 to 3% w/v. Some examples of appropriate chelating agents are, but not limited to, ethylene diamine tetraacetic acid (EDTA); ethylene glycol-bis(2-aminoethyl)-N,N,N',N'-tetraacetic acid (EGTA) and citric acid in the range of about 250 to 750 mM. Examples of appropriate reducing agents, include but are not limited to, tris(2-carboxyethyl)phosphine (TCEP) dithio-erythritol (DTE), and dithiothreitol (DTT) in the range of about 10 to 100 mM, prepared fresh prior to use. Some examples of appropriate enzymes are, but not limited to, caspase, chymotrypsin, pepsin, proteinase K, thrombin, *Staphylococcus* V8 protease, pronase, papain, *Bacillus* sp. E1A protease, and trypsin in the range of 0.5 to 10 mg/ml final concentration in the lysis solution. In some embodiments the lysis solution is prepared just before use by combining the chelating agent, at a pH of about 7.5 to 8.5 with detergent and salt, followed by adding the reducing agent solution and the enzyme.

In some embodiments, the chelating agent is prepared in a solution having the detergent with or without the salt, the reducing agent is freshly prepared, and the enzyme is in solution. The salt is either in solution or present in the detergent solution. The solutions can then be combined just prior to use to form the lysis solution. Alternatively, in some embodiments of the present teachings a lysis solution can be prepared and then freeze-dried. The freeze-dried lysis reagent can then be solubilized just prior to use. Such methods of freeze-drying are conventional and known to one of ordinary skill in the art. The result of a freshly prepared lysis solution is that the components have not degraded or oxidized such as may occur with prolonged storage or exposure to light and therefore decrease nucleic acid extraction and overall yield of nucleic acid. In some embodiments, the adhesive material or solid biological material is incubated at from about 50° C. to 70° C. for two hours to release cellular material from adhesive materials or solid biological matrices with 56° C. being a common temperature used. In some embodiments, the natural or synthetic material is incubated at from about 40° C. to 70° C. for 40 min to 1 hour. The extraction can be assisted by shaking. In some embodiments the lysis solution further comprises compounds to protect the released nucleic acids and maintain their compatibility for use in downstream assays such as, for example, PCR assays, and in particular DNA genotyping systems, for example STR assays.

Following incubation of the adhesive material, or solid biological sample, the sample can be centrifuged to pellet residual solid tissue, or adhesive material. The resulting supernatant product comprises nucleic acids. The supernatant is suitable for nucleic acid isolation and purification using methods known to one of ordinary skill in the art or commercial nucleic acid isolation and purification products such as the PrepFiler™ Kit. The kit can be use to remove cellular debris, residual contaminants and/or inhibitors of PCR.

In some embodiments of the present teachings, then, nucleic acid molecules can be isolated from solid matrices including biological samples including but not limited to: bone; cartilage; ligament; tendon; and tooth. In some embodiments, the biological sample is calcified, mummified, baked or otherwise in a natural or preserved state. In some embodiments, the solid biological sample is fragmented, crushed, pulverized or otherwise ground into a fine particulate, such as a powder. The yield of nucleic acid, such as DNA, is variable depending upon the age of the solid material, the amount of starting material and the degradation or preservation of the sample. The yield of the nucleic acid as DNA from bone and tooth samples is summarized in Table 1

The yield of DNA from 100 mg of long bone samples ranged from 0.25 to 2.15 ng, which is typical of such a sample type since each bone sample is unique in the content and state of biological material. The $C_T$ values for internal PCR control (IPC) determined by the Quantifiler® Human DNA Quantification Kit (Applied Biosystems) for the bone samples tested did not increase significantly compared to that for the non-template control (NTC, Table 1). If the DNA extract contained PCR inhibitors, typically an upward shift in $C_T$ value for the sample compared to the IPC $C_T$ value for the NTC would be expected (Applied Biosystems, Quantifiler® Human DNA Quantification Kit and Quantifiler® Y Human Male DNA Quantification Kit. User's Manual. PN 4344790 Rev. B, (2003)). Thus, the PCR inhibitors present in bone and tooth samples have been efficiently removed during the extraction of DNA using the lysis reagent solution followed by isolation and purification with the PrepFiler™ kit reagents.

TABLE 1

Yield of human DNA from bone and tooth

| Sample[a] | Description | Total Yield (ng) | IPC $C_T$ Value |
|---|---|---|---|
| Bone-1 | 100 mg long bone | 1.9 | 27.05 |
| Bone-2 | 100 mg long bone | 0.66 | 27.12 |
| Bone-3 | 100 mg long bone | 1.19 | 26.96 |
| Bone-4 | 100 mg long bone | 1.6 | 27.19 |
| Bone-5 | 100 mg long bone | 0.8 | 27.12 |
| Bone-6 | 100 mg long bone | 0.24 | 27.11 |
| Bone-7 | 100 mg long bone | 2.22 | 27.17 |
| Bone-CA | 50 mg clavicle bone | 7.95 ± 1.2 | 27.012 |
| Tooth | 10 mg | 450 ± 50 | 26.95 |
| Extraction Blank | | 0 | 26.80 |
| Non Template Control (NTC) | | NA[b] | NA[b] |

[a]Bone samples were of unknown age. Tooth sample was 1 year old.
[b]Not applicable.

The quantity of bone sample tested for optimum extraction and yield of nucleic acid varied from 50 mg to 200 mg and the volume of the lysis solution supernatant collected was adjusted, whenever necessary, to 200 μL using PrepFiler™ lysis buffer prior to isolation of DNA. The total yield of DNA was almost doubled when the quantity of bone powder was increased from 25 to 50 mg powder (Table 2). Further increase in the quantity of bone powder increased the yield of DNA but the incremental increase in the yield of DNA was not proportional to the quantity of bone powder. The evaluation was conducted in triplicate. The volume of lysis solution supernatant recovered after incubation of 200 mg of bone powder was 130 μL compared to 200 μL from 50 mg of bone powder. Therefore, processing of bone powder greater than 200 mg did not appreciably increase DNA yield.

TABLE 2

| Bone-CA (mg) | Total Yield (ng) | Yield/g bone | IPC $C_T$ Value |
|---|---|---|---|
| 25 | 4.8 ± 1 | 0.2 | 27.05 |
| 50 | 9.3 ± 3 | 0.18 | 26.94 |
| 100 | 12.0 ± 3 | 0.12 | 27.03 |
| 200 | 21.6 ± 6 | 0.11 | 26.89 |

TABLE 2-continued

| Bone-CA (mg) | Total Yield (ng) | Yield/g bone | IPC $C_T$ Value |
|---|---|---|---|
| Extraction Blank | 0 | NA | NA |
| Non Template Control (NTC) | NA | NA | 26.85 |

The extent of extraction of nucleic acid material from bone samples was investigated at different time intervals from 1 to 18 hours. 50 mg of bone was extracted in triplicate. The yield of DNA is summarized in Table 3. The yield of DNA increased by 1.54 fold when the time for extraction of the bone sample with the lysis solution was increased from 1 to 2 hours. However, further increase in the incubation time to 18 hours did not increase the yield of DNA substantially. However, incubation time up to 18 hours did not affect the extraction adversely.

TABLE 3

| Time for lysis (hours) | Total Yield (ng) | IPC $C_T$ Value |
|---|---|---|
| 1 | 5.2 ± 1 | 27.132 |
| 2 | 8.0 ± 1 | 27.047 |
| 4 | 8.5 ± 1.5 | 26.952 |
| 8 | 8.8 ± 1.5 | 26.913 |
| 18 | 11.4 ± 1 | 26.923 |
| Non Template Control (NTC) | NA | 26.815 |

DNA extracts from seven long bone samples (bone 1 through 7) were processed for STR analysis using AmpFlstr® Identifiler® and MiniFiler™ kits (Applied Biosystems), following the manufactures protocol. The results are summarized in Table 4. The Identifiler Kits amplifies a total of 16 STR loci and the MiniFiler kit amplifies 9 STR loci. In each sample tested, conclusive loci are compared to the total amplifiable loci for each of the kits. Bone-4 sample provided a complete STR profile using both kits. Bone-6 did not provide results when amplified using the Identifiler® kit but provided amplification of only 4 loci using the MiniFiler™ kit. All other bone samples tested provided complete STR profiles with the MiniFiler™ kit and partial STR profiles with the Identifiler® kit. The MiniFiler™ kit is designed to obtain profiles from degraded DNA samples (J. J. Mulero, et al., J. Forensic Sci. (2008) 53:838-852). The results indicate that the bone samples were aged and degraded to different extent.

TABLE 4

| Sample[a] | Identifiler ® Kit | MiniFiler ™ Kit |
|---|---|---|
| Bone-1 | 9/16 | 9/9 |
| Bone-2 | 9/16 | 9/9 |
| Bone-3 | 10/16 | 9/9 |
| Bone-4 | 16/16 | 9/9 |
| Bone-5 | 9/16 | 9/9 |
| Bone-6 | 0/16 | 4/9 |
| Bone-7 | 15/16 | 9/9 |

[a]Bone samples were of unknown age.

In some embodiments, the present teachings include using a plurality of samples ranging from when only trace amounts of biological material is potentially present. The sample amount can range from 50 to 200 mg of calcified tissue or solid biological sample in each tube and then the supernatants are combined and concentrating by standard methods prior to isolation and purification.

In some embodiments of the present teachings, then, nucleic acid molecules can be isolated from adhesive materials, including, but not limited to: chewing gum; cigar butt; cigarette butt; adhesive film; adhesive label; adhesive paper; adhesive skin patch; envelope flap, stamp, and dried blood, dried saliva, environmental sampling, including but not limited to dust, soil, dirt and a fingerprint via an adhesive tape lift, and adhesive tape. In some embodiments, the adhesive skin patch includes, but is not limited to: EEG or EKG electronic electrode; transferable tattoo; transdermal chemical substance patch and wound care dressing. In some embodiments, the adhesive tape includes, but is not limited to: tape; athletic tape; forensic tape; and so on. In some embodiments, the adhesive paper includes, but is not limited to envelope, removable paper, stamp and so on.

Comparisons of DNA yields from samples containing adhesives such as cigarette butts, chewing gum, tape lifts, envelopes, and stamps using the disclosed lysis reagent solution, PrepFiler™ lysis buffer and the EZ1 DNA Investigator Kit (Qiagen, Valencia, Calif.) are shown in Table 5. In general, the yields of DNA using the disclosed lysis reagent solution were higher for tape lift and cigarette butts samples compared to the yields obtained using the PrepFiler™ lysis buffer. Similarly, the yield of DNA for two of the three chewing gum samples tested was higher using the disclosed lysis reagent solution. Samples were generally of similar quantities of biological material (see Examples I and IV). Because the evaluations involved using real-world sample types as would be encountered in forensics laboratories, the sample types were not absolutely uniform. Thus, the resulting yields of DNA are useful as a measure of the overall performance of the lysis reagent solution. It has been observed that the tape lift and chewing gum samples each release a large amount of adhesive when the PrepFiler lysis buffer was used. For the tape lift samples, some of the clumps of the adhesive could be removed before further PrepFiler protocol processing however, in many of the samples, the magnetic particles did not form a pellet and some of the samples had to be centrifuged during PrepFiler protocol wash steps. The lysis reagent solution had a much smaller amount of the adhesive released during the extraction process. Consequently, the magnetic particles formed stronger pellets during the subsequent PrepFiler wash steps leading to improved nucleic acid recovery, including DNA yields. Small pieces of paper were removed by centrifugation from the cigarette samples. The Sherman brand cigarette paper is purple and it was observed that the purple dye was released under the PrepFiler™ lysis conditions. Additionally, the IPC $C_T$ values for all case type samples studied were similar to that obtained for NTC indicating effective removal of PCR inhibitors from the biological samples and substrates (Table 5).

TABLE 5

STR profile results from long bone samples[a]

| | | Lysis Reagent Soln. | | PrepFiler™ Lysis | |
|---|---|---|---|---|---|
| Substrate | Sample | Total DNA Yield (ng)[a] | IPC $C_T$ | Total DNA Yield (ng) | IPC $C_T$ |
| Tape lifts | Tape + 2 μL blood[b] | 40 | 26.6 | 14 | 27.4 |
| | Tape lift of 2 μL blood | 20 | 27.3 | 17 | 27 |
| | Tape + 5 μL saliva[b] | 143 | 27.1 | 64 | 26.8 |
| | Tape lift of 5 μL saliva | 7 | 26.9 | 3 | 27.4 |
| | Tape lift, shirt cuff | 0.6 | 26.6 | ND[c] | ND |
| | Tape lift, shirt cuff | 4 | 26.7 | ND | ND |
| | Tape lift, shirt collar | 2.5 | 26.8 | ND | ND |
| | Tape lift, shirt collar | 0.6 | 26.9 | ND | ND |
| | Substrate Blank | 0 | 26.8 | 0 | 26.8 |
| | Extraction Blank | 0 | 27.0 | 0 | 27.0 |
| Chewing Gum[d] | Winterfresh | 7 | 27.0 | 15 | 26.4 |
| | Doublemint | 6 | 27.1 | 3 | 27.3 |
| | Orbit | 20 | 27.1 | 19 | 26.6 |
| | Extra White | 27 | 28.1 | ND | ND |
| | Airwave (2 min. chewed) | 7 | 27.8 | ND | ND |
| | Airwave (40 min. chewed) | 30 | 27.7 | ND | ND |
| | Blast Mentos Berry-Lime | 30 | 27.7 | ND | ND |
| | Extraction Blank | 0 | 27.1 | 0 | 27.1 |
| Cigarette Butts | Marlboro | 174 | 26.7 | 25 | 27.6 |
| | Marlboro Menthol Light | 75 | 26.7 | 39 | 27.1 |
| | Sherman | 424 | 26.6 | 111 | 29.0 |
| | Gauloises Menthol | 76 | 26.7 | 22 | 28.0 |
| | Marlboro Menthol Light[e] | 35 | 26.7 | 3 | 26.8 |
| | Holiday Gold | 12 | 26.9 | ND | ND |
| | Holiday Menthol | 37 | 26.5 | ND | ND |
| | Substrate Blank | 0 | 26.7 | 0 | 26.7 |
| | Extraction Blank | 0 | 26.7 | 0 | 26.7 |

[a] Elution volume was 50 μL. The quantities presented are average values.
[b] 2 μL of blood or 5 μL of saliva was added directly to the 1.5 cm × 2.5 cm piece of tape.
[c] Not determined
[d] ⅛ of a piece of gum processed, all are Wrigley's brand except Blast Mentos Berry-Lime
[e] Weathered sample-left outside for 72 hr before analysis. 72 hr temperature range was 4-15° C.

In some embodiments of the present teachings, a Tris-Cl Lysis Solution can used to isolate nucleic acid molecules from denim materials containing on the surface or embedded within a biological fluid sample including but not limited to, for example, hair, feces, blood, tissue, urine, saliva, cheek cells, vaginal cells, skin, for example skin cells contained in fingerprints, buccal sample, amniotic fluid containing placental cells, and amniotic fluid containing fetal cells, and semen. The biological fluid can be moist, wet, dried or adherent to the denim material. In some embodiments, the biological fluid sample can be found within an environmental sample such as soil. In other embodiments, disclosed are methods for extracting a biological fluid material from denim material simultaneously with lysing the cells within the biological fluid material and eluting the nucleic acid from the substrate. In some embodiments, the method can also include heating or incubating a Tris-Cl lysis solution with the denim substrate containing the biological fluid material. In some embodiments, the Tris-Cl lysis solution is centrifuged to separate the nucleic acid containing lysate from the substrate.

In some embodiments of the present teachings, compositions are provided wherein a sample can be treated with a Tris-Cl lysis solution comprising Tris-chloride (Tris-Cl), at least one each of a detergent, a chelating agent, a reducing agent, and an enzyme, and combinations thereof in order to extract nucleic acid molecules from the denim substrate sample. The detergent can be one or more of N-lauroyl sarcosine, sodium deoxycholate, CTAB, dodecyl β-D-maltoside, nonanoyl-N-methylglucamide, polyethylene glycol p-(1,1,3,3-tetramethylbutyl)-phenyl ether, sodium dodecyl sulfate (SDS), and combinations thereof. The chelating agent can be one or more of ethylene glycol tetraacetic acid (EGTA) and ethylene diamine tetraacetic acid (EDTA), citric acid and combinations thereof. The reducing agent can be one or more of tris(2-carboxyethyl) phosphine (TCEP) dithioerythritol (DTE), and dithiothreitol (DTT). The enzyme can be one or more of caspase, chymotrypsin, pepsin, proteinase K, thrombin, Staphylococcus V8 protease, pronase, papain, Bacillus sp. E1A protease, and trypsin. The salt can be one or more of sodium chloride, potassium chloride, magnesium chloride, manganise chloride as well as fluorinated and iodinated forms thereof. The lysis solution can have a pH ranging from 5.0-12.0, or 5.1, 6.0, 7.0, 8.0, 9.0, 10.0, and 11.0 as well as intervals within each whole number.

In some embodiments, the sample can comprise nucleic acid extracted from denim materials including, but not limited to, denim fabric including blue, dark blue, black, stone-washed, acid washed and the like. In additional embodiments of the present teachings, methods are described wherein a nucleic acid can be extracted from a sample, comprising the steps of incubating the sample with a solution comprising Tris-Cl, one or more of a detergent, a chelating agent, a reducing agent, a salt and an enzyme; and extracting the supernatant. The incubation can be at room temperature, 35° C., 40° C., 41° C., 42° C., 43° C., 44° C., 45° C., 50° C., 51° C., 52° C., 53° C., 54° C., 55° C., 56° C., 57° C., 58° C., 59° C., 60° C., 65° C. and 70° C., as well as intervals therein. Such methods may further comprise the steps of centrifuging the incubation solution to remove solids from the supernatant and treating the supernatant to isolate the nucleic acids.

In some embodiments, inhibitors of PCR can be extracted or released into the lysate or eluate during the process of nucleic acid extraction resulting in poor quality DNA. The quality of the nucleic acid extracted or recovered from a biological fluid sample can adversely impact analysis of the nucleic acid in processes such as, for example, quantification, detection, and genotyping of specific nucleic acids or a biological species.

In some embodiments, the Tris-Cl can be at a concentration of from 10 mM to 600 mM and at a pH of from 5 to 12. In some embodiments, the detergent can be present at from 0.1% to 5.0% and the chelating agent can be present at from about 1.0 mM to 600 mM at a pH of from 7.0 to 8.5 (adjusting pH with 0.5-1M NaOH). Some examples of appropriate salts include, but are not limited to, sodium chloride, potassium chloride, magnesium chloride, manganese chloride as well as fluorinated and iodinated forms thereof in the range of about 1 mM to 1 M. In some embodiments, the enzyme concentration is in the range of 1 mg/uL to 50 mg/mL and the reducing agent concentration is in the range of 10 mM to 1 M.

Figure 1:
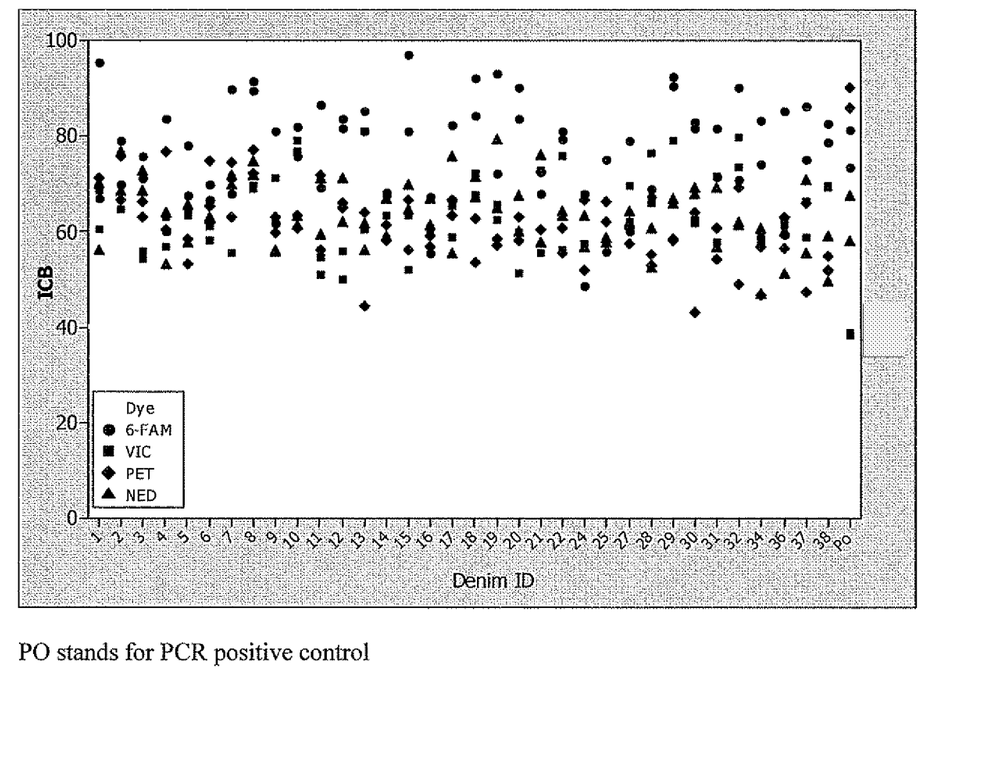
FIG. 1 is a graph depicting the Intercolor balance (ICB) between STR alleles for blood replicates extracted from denim. ICB was calculated by dividing maximum peak height by minimum peak height in each color (heterozygotes peaks are average and homozygotes divided by 2). Samples are listed in Table 6.

Various types, weights and colors of denim fabric (obtained from Jo-Ann's Fabrics, San Mateo, Calif.) were used to analyze the Tris-Cl lysis reagent solutions. Basically, blood was applied to each denim type and a 5 mm denim punch was removed from the center of the blood spot, approximating 1 uL of dried blood. Comparisons of Intercolor Balance (ICB) using the Identifiler® kit (Applied Biosystems) on DNA recovered from the denim samples listed in Table 6, some of which contained indigo dye, acid wash treatment, stone wash treatment, ice wash treatment, black dye, texture, printing and of varying weights and finishes is disclosed in FIG. 1 following using nucleic acid extraction with the disclosed Tris-Cl-buffered lysis reagent solution, PrepFiler™ lysis buffer and Identifiler® kit (Applied Biosystems). In general, the DNA quality using the disclosed Tris-Cl-buffered lysis reagent solution were sufficient to obtained full STR profiles for each sample tested. These results show that the disclosed Tris-Cl-buffered lysis reagent solution can provide high quality nucleic acid even in the presence of indigo, black dye, and chemical treatments, known PCR inhibitors.

TABLE 6

| Denim ID | Description |
| --- | --- |
| 1 | 10 OZ Distressed STR |
| 2 | 10.5 OZ DK blue stove |
| 3 | 5.8 OZ sun-bleached DNM |
| 4 | 9 OZ DK blue stovepipe |
| 5 | 8 OZ blue stovepipe D |
| 6 | 4 OZ DK blue denim |
| 7 | 8 OZ DK blue denim |
| 8 | 8 OZ indigo stovepipe |
| 9 | 9.9 OZ blue textured st |
| 10 | 11 OZ black STR denim |
| 11 | 5 OZ blue xhatch denim |
| 12 | 12. L BL ice wsh |
| 13 | 8 OZ dirty xhatch denim |
| 14 | 10 OZ indigo wash denim |
| 15 | 10 OZ LT blue STR sto |
| 16 | 10.5 OZ med blue xhat |
| 17 | 9.75 OZ lt blue stove |
| 18 | 7 OZ blue STR stovepipe |
| 19 | 10 OZ sbl wash denim |
| 20 | 5 OZ blue xhatch denim |

TABLE 6-continued

| Denim ID | Description |
| --- | --- |
| 21 | 9 OZ blue textured st |
| 22 | 9 OZ med blue str denim |
| 24 | 6.5 OZ indigo denim |
| 25 | 7 OZ lt blue slub denim |
| 27 | sbl wsh denim 10 OZ |
| 28 | 28. ind brush denim |
| 29 | 10 OZ distressed nost |
| 30 | 12.5 OZ nostalgic str |
| 31 | 4 OZ lt blue denim |
| 32 | 11 OZ lt blue str denim |
| 34 | 4 OZ lt blue denim |
| 36 | 7 OZ blue denim |
| 37 | 9 OZ indigo shine was |
| 38 | 7 OZ blue str stovepipe |

In some embodiments of the present teachings, then, nucleic acid molecules can be isolated from denim using Tris-Cl-buffered lysis reagent solution.

A capillary electrophoresis electron micrograph of STR profiles obtained from bone, tooth and some adhesive containing materials were typical of such sample types. Furthermore, the STR profiles demonstrated that the DNA obtained was free of any PCR inhibitors (data not shown, Stray et al., Forensic Science International: Genetics Supplement Series 2 (2009) 159-160, incorporated by reference herein). The lysis reagent solution was shown to disrupt calcified tissue matrices, achieve effective DNA extraction from pulverized bone and tooth samples as well as from adhesive materials such as tape, chewing gum, envelope, stamp and cigarette butts The results for denim materials for the STR profiles demonstrated that the DNA obtained was free of any PCR as shown in FIGS. 1-4. The Tris-Cl-buffered lysis reagent solution was shown to achieve effective DNA extraction from denim samples. Both the lysis reagent solution and the Tris-Cl-buffered lysis reagent solution resulted in improved recovery of nucleic acid, improved DNA isolation, purification and the DNA was absent interfering materials and impurities that would compromise or impede further analyses such as PCR, real-time PCR and STR profiling.

In other embodiments of the present teachings, the nucleic acid recovered from a fingerprint using the methods described herein can be used for identification of the organism from which the biological material or biological sample containing the nucleic acid was obtained as discussed supra. In conjunction with or separate to the nucleic acid identification assays the fingerprint image can be used for comparison to a forensic database including but not limited to a fingerprint collection and/or a database of fingerprints. Fingerprints are a well-established forensic identification tool and numerous fingerprint databases and collections exist worldwide for purposes of identification and confirmation/verification of identity. The advantage of utilizing nucleic acid obtained from a fingerprint provides further confirmatory and conclusive evidence of identification and further, association of an identified individual with the surface and so the place or object from which the fingerprint nucleic acid was obtained.

In other embodiments of the present teaching, the nucleic acid recovered from denim using the methods described herein can be used for identification of the organism from which the biological material or biological sample containing the nucleic acid was obtained as discussed supra.

The present teachings are also directed to kits for extraction of nucleic acid from a matrix, including, but not limited to, a biological material that is calcified or otherwise hardened to a solid state, an adhesive or sticky materials thought to contain nucleic acid and denim thought to contain nucleic acid. Such kits can be utilized for archeological, criminal, forensic, human identification, and research that utilize the methods described above. In some embodiments, a basic kit can comprise a container having a lysis solution capable of releasing nucleic acid from a matrix, an adhesive and/or sticky material or denim material. A kit can also optionally comprise instructions for use. The kit can also comprise other optional kit components, such as, for example, a solution comprising a polymer and detergent, magnetically attractable particles, one or more wash solutions, a nucleic acid elution solution, a nucleic acid extraction control, a magnetic device, and a protocol and manual to educate the user and limit error in use. The amounts of the various reagents, tubes and magnetic device(s) in the kits also can be varied depending upon a number of factors, such as the optimum purification and/or sensitivity of the process. It is within the scope of these teachings to provide test kits for use in manual applications or test kits for use with automated sample preparation, reaction set-up, detectors or analyzers.

Those in the art understand that the detection techniques employed are generally not limiting. Rather, a wide variety of nucleic acid extraction means are within the scope of the disclosed compositions, methods and kits, provided that the material being analyzed contains nucleic acid or has nucleic acid adhered to the material.

While the principles of this invention have been described in connection with specific embodiments, it should be understood clearly that these descriptions are made only by way of example and are not intended to limit the scope of the invention. What has been disclosed herein has been provided for the purposes of illustration and description. It is not intended to be exhaustive or to limit what is disclosed to the precise forms described. Many modifications and variations will be apparent to the practitioner skilled in the art. What is disclosed was chosen and described in order to best explain the principles and practical application of the disclosed embodiments of the art described, thereby enabling others skilled in the art to understand the various embodiments and various modifications that are suited to the particular use contemplated. It is intended that the scope of what is disclosed be defined by the following claims and their equivalence.

Aspects of the present teachings may be further understood in light of the following examples, which should not be construed as limiting the scope of the present teachings in any way.

Examples

Those having ordinary skill in the art will understand that many modifications, alternatives, and equivalents are possible. All such modifications, alternatives, and equivalents are intended to be encompassed herein.

The following procedures are representative of reagents and procedures that can be employed for the extraction of nucleic acids from solid biological matrices and adhesive substrates suspected of containing nucleic acid.

I. Sample Pre-Treatment

Bone and tooth samples were cleaned using mild detergent solution, overnight air drying, and removing the exterior layer using a sanding stone attached to a Dremel tool Dremel, Madison, Wis.). Larger pieces of bones were chopped into small pieces. Pieces of bone and tooth were pulverized using a fresh or cleaned grinder (e.g., a Cryomill, BioSpect Products, Bartlesville, Okla.). Pulverized bone or tooth power was stored at room temperature.

Smoked cigarette butts were stored at room temperature. The filter material was removed and the first 5 mm of the bottom portion of the paper, which comes into contact with skin (i.e., finger and mouth) was cut into three pieces.

Chewed chewing gum samples were stored at room temperature. The gum was flattened (~3 mm thick) in a clean Petri dish. The lid was closed and the Petri dish was stored at −80° C. for several hours for hardening. The hardened gum was cut into 8 equal sized portions. One portion of the gum was used for extraction of DNA.

Tape lift samples from various sources were prepared. From each sample, a 1.5 cm×2.5 cm piece of tape (containing the biological sample) was used for processing. The blood or saliva was dry before removing by a tape lift procedure and then adding the lysis reagent solution. For the tape+biological fluid samples, 0.5-5 µL of blood or saliva was added directly to the adhesive side of the tape. For the tape lift samples, 2 µL of human blood or 5 µL of saliva was added to a glass slide. Once the biological material was dry, the biological material was tape lifted. Tape lift samples containing skin cells were also collected from either the inside of a shirt collar or the inside of a shirt cuff from worn shirt samples.

Denim fabric samples (non-black denim) were prepared. 1 uL of blood in replicates of 4 were obtained using a 5 mm punch where blood had been applied and allowed to air dry. The lysis reaction with the Tris-Cl-buffered lysis reagent solution was carried out in a LySep™ column (Applied Biosystems) in a 500 uL volume in the presence of 3 uL reducing agent (1 M) and 3 uL 20 mg/mL enzyme. The column was incubated for 40 min at 56° C. on a thermal mixer. DNA extraction was done using the AutoMate Express™ (Applied Biosystems) following the manufacturers recommended protocol. DNA quantification was done using Quantifiler Duo™ kit (Applied Biosystems) following the manufacture's instructions. STR profiling was performed using the Identifiler Kit following the manufacture's instructions and CE analysis was performed on the Applied Biosystems 3130xl following the manufacture's instructions.

Denim fabric samples prepared with 20 uL of buccal epithelial cells in 6 replicates were analyzed as described for blood on denim. Blood on black denim was 2 uL of blood in 3 replicates and was analyzed as described for denim above.

II. Preparation of Lysis Reagent Solution

Sufficient quantity of Lysis solution was prepared to process a number of samples in duplicate or triplicate. The solution was freshly prepared by mixing 220 µL of 250-500 mM of chelating agent, pH 7.9 to 8.5 containing 1% w/v of at least one detergent to which was added 0.5-1 mg/mL enzyme and freshly prepared reducing agent in DNase free water at a final concentration of 10-100 mM. The lysis mixtures were incubated with or without shaking at a temperature in the range of approximately 50-70° C. for a period of 90 minutes to 2 hours. Table 6 illustrates lysis solutions that can be used to extract nucleic acid from solid biological materials and adhesive materials containing or thought to contain biological samples containing nucleic acid.

III. Preparation of Tris-Cl-Buffered Lysis Reagent Solution

Sufficient quantity of Tris-Cl-buffered lysis reagent solution was prepared to process a number of samples in duplicate, triplicate or 6-replicates. The solution was freshly prepared by mixing 220 µL of 250-1000 mM of chelating agent, pH 7.9 to 8.5 containing 0.5-3% w/v of at least one detergent to which was added 0.5-50 mg/mL enzyme and freshly prepared reducing agent in DNase free water at a final concentration of 10-100 mM. The lysis mixtures were incubated with or without shaking at a temperature in the range of approximately 50-70° C. for a period of 90 minutes to 2 hours.

TABLE 6

Lysis Solutions

| Component | Formulation I | Formulation II | Formulation III | Formulation IV |
|---|---|---|---|---|
| EGTA | 250 to 500 mM | 0 | 250 to 500 mM | 0 |
| EDTA | 0 | 250 to 500 mM | 0 | 250 to 500 mM |
| DTT | 10 to 100 mM | 10 to 100 mM | 10 to 100 mM | 10 to 100 mM |
| NLS | 0.5 to 3% w/v | 0.5 to 3% w/v | 0 | 0 |
| Sodium Deoxycholte | 0 | 0 | 0.5 to 3% w/v | 0.5 to 3% w/v |
| SDS | 0 | 0 | 0 | 0 |
| Sodium Citrate | 0 | 0 | 0 | 0 |
| Triton X 100 | 0 | 0 | 0 | 0 |
| NP-40 | 0 | 0 | 0 | 0 |
| Proteinase K | 0.5 to 1 mg/mL | 0.5 to 1 mg/mL | 0.5 to 1 mg/mL | 0.5 to 1 mg/mL |

| Component | Formulation V | Formulation VI | Formulation VII |
|---|---|---|---|
| EGTA | 250 to 500 mM | 250 to 500 mM | 250 to 500 mM |
| EDTA | 0 | 0 | 0 |
| DTT | 10 to 100 mM | 10 to 100 mM | 10 to 100 mM |
| NLS | 0.5 to 3% w/v | 0 | 0 |
| Sodium Deoxycholte | 0.5 to 3% w/v | 0 | 0.5 to 3% w/v |
| SDS | 0 | 0.1 to 0.5% w/v | 0 |
| Sodium Citrate | 0 | 50 to 150 mM | 0 |
| Triton X 100 | 0 | 0.1 to 0.3% v/v | 0 |
| NP-40 | 0 | 0 | 0.1 to 0.3% |
| Proteinase K | 0.5 to 1 mg/mL | 0.5 to 1 mg/mL | 0.5 to 1 mg/mL |

TABLE 7

Wash Solutions:

| Component | Wash Buffer A Final Concentration | Wash Buffer B Final Concentration |
|---|---|---|
| 10 mM Tris-Cl, pH 8.0 | | 4 mM |
| 0.1 mM EDTA | | 0.04 mM |
| 95% Ethanol | 70% | 60% |
| Sodium deoxcholate (DSD) | 0.5% | |
| Final Volume | 100 mL | 100 mL |

III. Extraction of Nucleic Acid from Solid Biological Samples

230 μL of freshly prepared Lysis solution was added to 50-200 mg of bone or 10 mg of tooth powder, in a 2.0 mL screw cap tube. The lid was closed and the tube was incubated at 56° C. in an Eppendorf® Thermomixer R (Eppendorf North America, Westbury, N.Y.), at 1100 rpm for 2 hours. At the end of incubation, the tube was centrifuged at 10,000×g for 5 min and clear supernatant/lysate (maximal of 210 μL) was transferred to a fresh 1.5 mL microfuge tube containing 300 μL of PrepFiler™ Lysis Buffer and processed for isolation of DNA according to the manufactures large volume protocol. Basically, 15 uL of PrepFiler™ Magnetic particles and 300 uL 99.5% Isopropanol is added followed by gentle mixing. The particles are was twice with PrepFiler™ Wash Buffer A using 600 uL and then 300 uL of Buffer A followed by one wash with 300 uL PrepFiler™ Wash Buffer B. The nucleic acid is then eluted into 50 uL of PrepFiler™ Elution Buffer as outlined in the PrepFiler Manual and PrepFiler Automated Forensic DNA Extraction Kit or the PrepFiler Manual Kit User Guide (P/N 4390932-01).

IV. Extraction of Nucleic Acid from Adhesive Materials 230 uL of freshly prepared Lysis solution was added to the adhesive containing samples prepared as described above in a 1.5 mL microfuge tube. The lid was closed and the tube was incubated at 56° C. in an Eppendorf Thermomixer R at 750 rpm for 40 min. At the end of incubation, the contents were transferred to a filter column (Axygen Scientific, Inc., Union City, Calif.). The supernatant/lysate was separated from the substrate by centrifuging the filter column for 2 min at 16,110×g. 300 μL of PrepFiler™ Lysis Buffer was added to the clear supernatant/lysate and processed for isolation of DNA according to the manufactures protocol.

V. Extraction of Nucleic Acid from Denim Materials 500 uL of freshly prepared Lysis solution was added to the biological (fluid) containing samples prepared as described above in a 1.5 mL LySep tube. The lid was closed and the tube was incubated at 56° C. in an Eppendorf Thermomixer R at 750 rpm for 40 min. The supernatant/lysate was separated from the substrate by centrifuging the LySep tube for 2 min at 16,110×g. 300 μL of PrepFiler™ Lysis Buffer was added to the clear supernatant/lysate and processed for isolation of DNA according to the manufactures protocol.

VI. Isolation of DNA

DNA from the lysate was isolated by following the large-sample protocol (for use with 500 μL of PrepFiler™ lysis buffer) as described by the manufacturer (Applied Biosystems, PrepFiler™ Forensic DNA Extraction Kit User Guide. PN 4390932 Rev. B, (2008)).

VII. Human DNA Quantification

The quantity of DNA was determined by Quantifiler® or Quantifiler DUO® Human DNA Quantification Kit (Applied Biosystems, Foster City, Calif.) using 2 μL of the DNA extract as described in the User's Manual (Applied Biosystems, Quantifiler® Human DNA Quantification Kit and Quantifiler® Y Human Male DNA Quantification Kit. User's Manual. PPN 4344790 Rev. B, (2003)). PCR was performed on the 7500 Real-Time PCR System and the data were analyzed using 7500 System SDS Software v1.2.3 (Applied Biosystems, Foster City, Calif.).

VIII. Short Tandem Repeat (STR) Analysis

The DNA extracts obtained from the biological samples using PrepFiler™ Forensic DNA Extraction Kit were amplified for Identifiler® kit analysis using the procedure described in the User's Manual (Applied Biosystems, AmpFlSTR® Identifiler® PCR amplification kit. User's Manual. PPN 4323291 Rev.B, (2001)). The amplified products were analyzed on a 3100 or 3130xl Genetic Analyzer (Applied Biosystems) using GeneMapper® ID Software v3.2.1 as described in the User Guides (Applied Biosystems, "ABI PRISM® 3100 Genetic Analyzer and ABI PRISM® 3100-Avant Genetic Analyzer. User Reference Guide" PN 4335393. RevA, (2002), Applied Biosystems, GeneMapper® ID software for human identification applications).

Although the present disclosure is described with respect to various embodiments and examples, various modifications may be made without departing from the spirit and scope of the invention.

What is claimed is:

1. A kit for extracting nucleic acid from a solid sample comprising: a lysis buffer comprising 250 to 500 mM ethylene glycol tetraacetic acid and further comprising each of the following: a detergent, a reducing agent, and an enzyme, wherein the detergent is selected from one or more of N-lauroyl sarcosine, sodium deoxycholate, cetyltrimethylammonium bromide, dodecyl β-D-maltoside, nonanoyl-N-methylglucamide, polyethylene glycol p-(1,1,3,3-tetramethylbutyl)-phenyl ether, and sodium dodecyl sulfate, wherein the reducing agent comprises one or more of tris(2-carboxyethyl)phosphine, dithioerythritol, and dithiothreitol, and wherein the enzyme is selected from caspase, chymotrypsin, pepsin, proteinase K, thrombin, *Staphylococcus* V8 protease, pronase, papain, *Bacillus* sp. E1A protease, trypsin and combinations thereof.

2. The kit of claim 1, wherein the solid sample is selected from a biological material and an adhesive material.

3. The kit of claim 1, optionally comprising: a solution comprising a polymer and detergent; and magnetically attractable particles.

4. The kit of claim 3, wherein the polymer comprises one or more of dextran, cellulose, cellulose derivatives, soluble starch, dextrin, cellodextrin, polyethylene glycol, heparin, glycogen, and combinations thereof.

* * * * *